United States Patent [19]

Rydell

[11] Patent Number: 4,758,223
[45] Date of Patent: Jul. 19, 1988

[54] INFLATION DEVICE FOR ANGIOPLASTY CATHETER

[75] Inventor: Mark A. Rydell, Golden Valley, Minn.

[73] Assignee: Schneider-Shiley (USA) Inc., Minneapolis, Minn.

[21] Appl. No.: 945,964

[22] Filed: Dec. 24, 1986

Related U.S. Application Data

[63] Continuation-in-part of Ser. No. 881,444, Jul. 2, 1986, abandoned.

[51] Int. Cl.$^4$ .......................................... A61M 29/00
[52] U.S. Cl. .................................. 604/98; 604/100; 604/191; 128/344
[58] Field of Search .................. 60/567; 222/135, 137, 222/387; 604/82, 88, 96–100, 236, 215, 218, 191; 128/344, 348.1

[56] References Cited

U.S. PATENT DOCUMENTS

| | | | |
|---|---|---|---|
| 3,467,096 | 9/1969 | Horn | 604/191 |
| 3,985,122 | 10/1976 | Topham | 604/82 |
| 4,439,185 | 3/1984 | Lundquist | 604/236 |
| 4,446,867 | 5/1984 | Leveen et al. | 604/97 |
| 4,476,866 | 10/1984 | Chin | 604/90 |
| 4,560,378 | 12/1985 | Weiland | 604/256 |
| 4,609,371 | 9/1986 | Pizzino | 604/191 |
| 4,610,666 | 9/1986 | Pizzino | 604/191 |

FOREIGN PATENT DOCUMENTS

| | | | |
|---|---|---|---|
| 0419869 | 10/1925 | Fed. Rep. of Germany | 604/82 |
| 1291859 | 4/1969 | Fed. Rep. of Germany | 604/82 |

Primary Examiner—Stephen C. Pellegrino
Assistant Examiner—Ralph Lewis
Attorney, Agent, or Firm—Orrin M. Haugen; Thomas J. Nikolai; Frederick W. Niebuhr

[57] ABSTRACT

A hand-operated device for inflating the expander on a balloon-type catheter and for perfusing fluids through the catheter and out its distal end. The inflator device comprises a housing containing a relatively large diameter and volume syringe and a relatively small diameter and volume syringe and a three-way valve for selectively controlling the fluid flow from the large syringe into the small syringe, from the large syringe into the lumen of the catheter or from the small syringe into the lumen of the catheter. By incorporating the two syringes in the same housing, a large volume of fluid, such as a radiopaque contrast medium, can be injected through the catheter and out its distal end while the small diameter and volume syringe can be used to pressurize the expander with considerably less effort than if the large diameter syringe had been used.

6 Claims, 3 Drawing Sheets

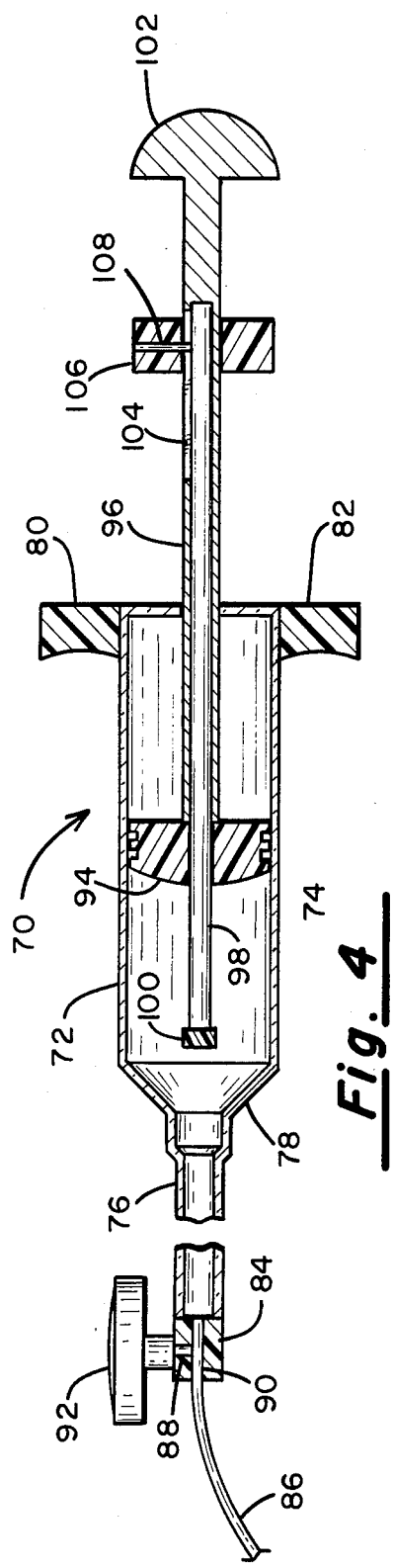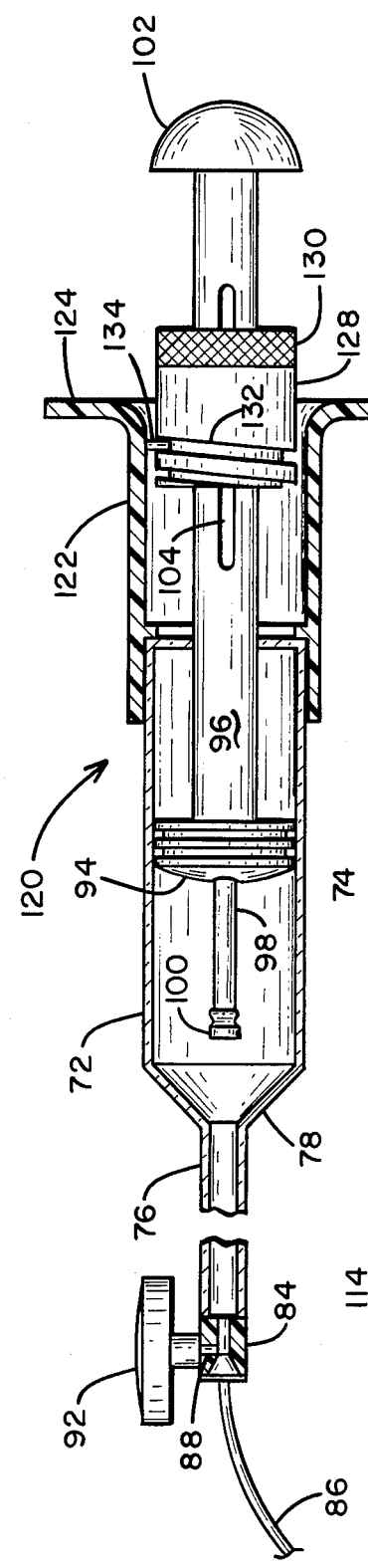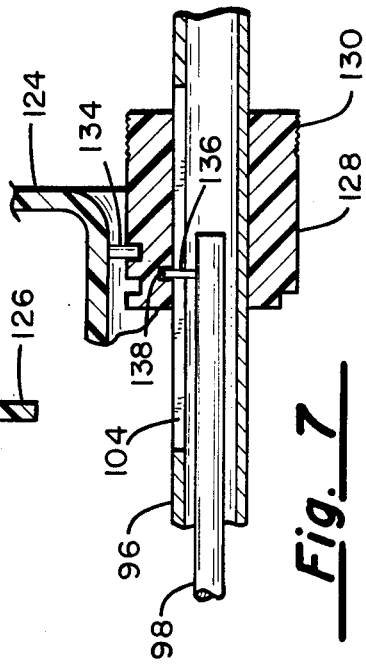

INFLATION DEVICE FOR ANGIOPLASTY CATHETER

CROSS-REFERENCE TO RELATED APPLICATION

This application is a continuation-in-part of application Ser. No. 881,444, filed July 2, 1986, now abandoned.

BACKGROUND OF THE INVENTION

I. Field of the Invention:

This invention relates generally to apparatus for performing angioplasty procedures for opening partially occluded blood vessels, and more particularly to a hand-operated inflation and fluid dispensing device adapted to be connected to the proximal end of angioplasty catheter for either inflating the expander member on the catheter or supplying a radiopaque contrast medium through the catheter and out its distal end.

II. Discussion of the Prior Art:

There is described in the Schjeldahl et al U.S. Pat. No. 4,413,989 the configuration of an angioplasty catheter specifically adapted to treat stenotic lesions located in one of the coronary arteries. Basically, the catheter comprises an elongated tubular member having a non-distensible expander member disposed proximate its distal end, the expander member being inflatable by introducing a fluid through the proximal end of the catheter whereby it flows through the lumen of the catheter and out one or more ports in the side wall of the tubular member which is surrounded by the expander member.

In treating stenotic lesions, it is often necessary to pressurize the expander member to a pressure in the range of from 7 to 10 atmospheres or more. This pressure must be sustained for periods of up to 30 seconds or more.

There is currently on the market an angioplasty catheter inflation device in the form of a molded plastic housing configured to contain a hypodermic-type syringe having a diameter of about 6.5 cms. and whose output port is coupled to the proximal end of the tubular catheter body. The plunger of the syringe is suitably positioned relative to integrally molded finger grips on the housing so that the plunger will fit in the palm of the hand as the user's fingers wrap about the finger grips. By squeezing, fluid is ejected from the syringe and through the elongated catheter so as to inflate the expander member. The device is constructed in accordance with the Lundquist U.S. Pat. No. 4,439,185 assigned to Advanced Cardiovascular Systems, Inc. of Mountain View, Calif. Using this prior art device, however, it is extremely difficult for the cardiologist or technician to sustain the necessary pressures for the time interval during which the expander is pressurized. It requires a very strong grip and often it is difficult to hold the device steady, and at the desired inflation pressure due to the strong force which must be applied to the inflation device. While the applied force can be reduced by reducing the overall diameter of the syringe's piston, this necessarily reduces the volume of fluid available to, for example, initially fill the lumen of the catheter and the expander with fluid or to later inject contrast media when the site being treated is to be inspected using fluoroscopic techniques.

SUMMARY OF THE INVENTION

In accordance with the present invention, the foregoing short-comings of the prior art inflators have been eliminated by conveniently incorporating in a single housing a pair of syringes, one being of a relatively large diameter and volume with the other being of significantly smaller diameter and volume. In a first disclosed embodiment, the output ports of the two syringes are fed through a three-way valve and when the valve is in a first disposition, fluid may be transferred from the large volume syringe into the smaller volume syringe and, thus, the large syringe acts as a storage reservoir. In a second position of the valve, the large volume syringe is in fluid communication with the lumen of the catheter and can be used to initially fill the catheter with fluid or later to supply a predetermined volume of contrast media to the distal end of the catheter. When the valve is in its third position, the small volume, small diameter syring has its outlet in fluid communication with the lumen of the catheter and, now, when the plunger of that small diameter syringe is depressed, relatively high pressures can be developed to inflate the expander member to a desired pressure, assuming the catheter had first been filled with fluid from the first syringe.

In accordance with a second disclosed embodiment, the inflation device comprises first and second coaxially disposed plunger operated pistons contained within a tubular syringe housing where the housing comprises a first, relatively large diameter tubular syringe portion and an integrally joined second tubular syringe portion of a lesser diameter. The coaxially disposed pistons are of appropriate diameter so as to respectively cooperate with the cylindrical walls of the two syringe portions. When initially filling the angioplasty catheter, the contents of the larger diameter syringe portion can be forced through the catheter by depressing a first plunger coupled to the larger diameter piston and once the volume of the catheter has been thus filled, the pressure in the dilation expander member can be increased by manipulating the piston cooperating with the syringe portion of smaller diameter.

OBJECTS

It is accordingly a principal object of the present invention to provide an improved inflation device for a transluminal angioplasty catheter.

Another object of the invention is to provide an inflation device for alternatively allowing relatively low pressure and large volume flow of fluid through the lumen of a transluminal angioplasty catheter or a high pressure within the catheter's expander member.

Yet another object of the invention is to provide a convenient hand-held device which can be used to introduce relatively high pressures within the expander member of a transluminal angioplasty catheter without requiring the application of undue force by the user.

Yet a further object of the invention is to provide a hand-held device adapted to be coupled to the proximal end of a transluminal angioplasty catheter for allowing the cardiologist to maintain a relatively high pressure within the catheter's expander without overtaxing his hand muscles.

These and other objects and advantages of the invention will become apparent to those skilled in the art from the following detailed description of a preferred embodiment, especially when considered in conjunc-

DESCRIPTION OF THE DRAWINGS

FIG. 4 is a cross-sectional view of a second preferred embodiment of the invention;

FIG. 5 is a view showing the constructional features of a piston used in the embodiment of FIG. 4;

FIG. 6 is a cross-sectional view of a third preferred embodiment of the invention; and FIG. 7 is an enlarged cross-sectional view of a portion of the embodiment of FIG. 6.

DESCRIPTION OF THE PREFERRED EMBODIMENTS

Figure 1:
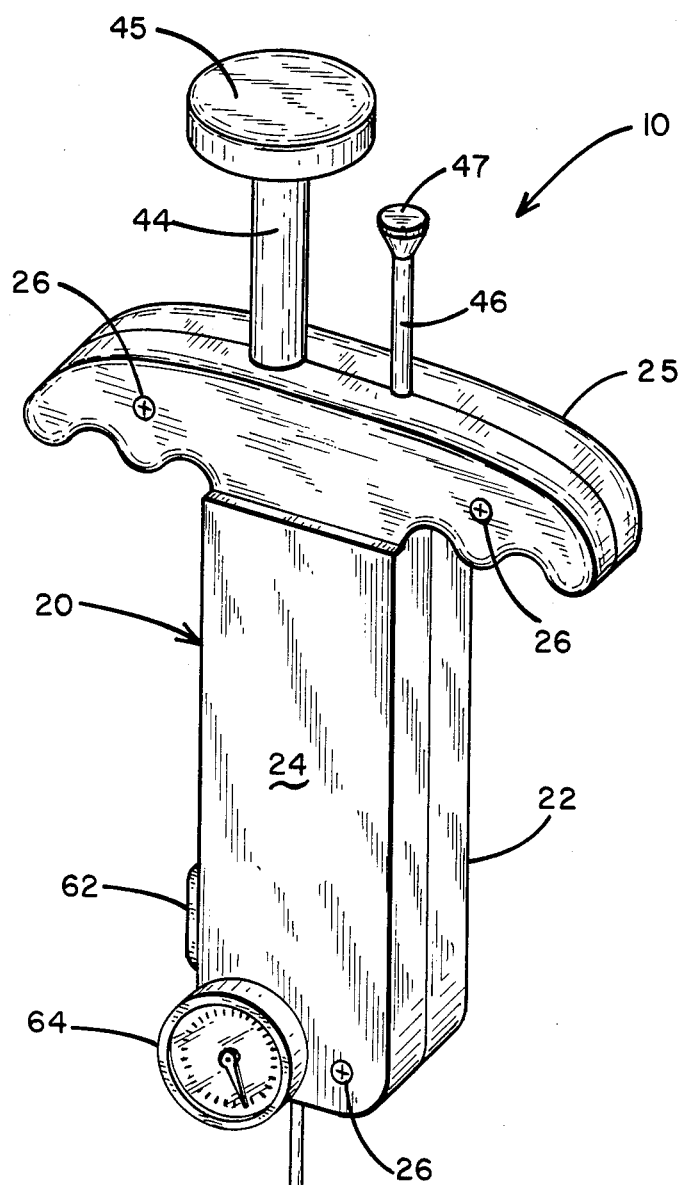
FIG. 1 is a perspective view of a first preferred embodiment.
Figure 2:
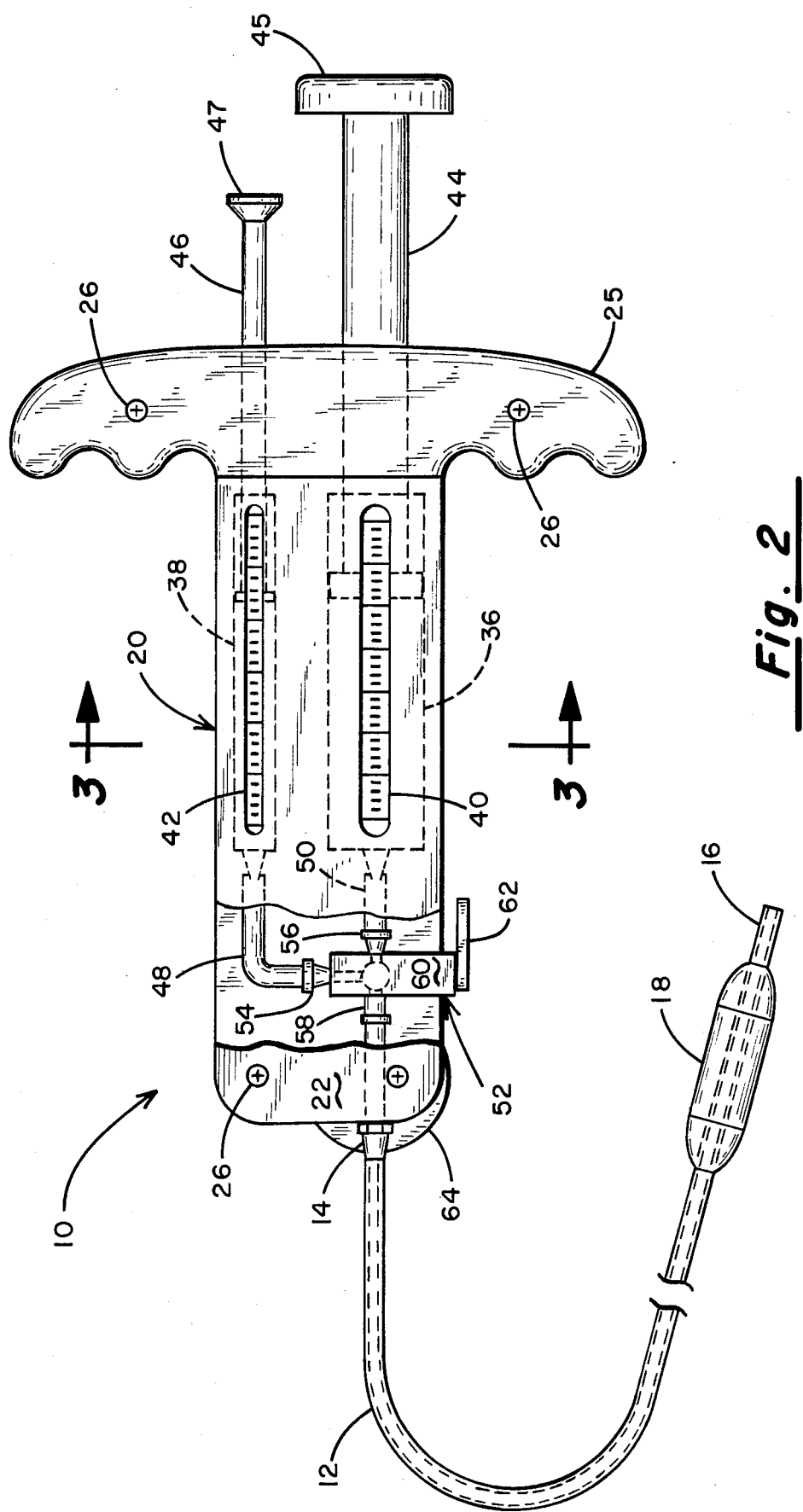
FIG. 2 is a front elevation of the embodiment of FIG. 1.

Referring first to FIGS. 1 and 2, there is indicated generally by numeral 10 an inflation device for a transluminal angioplasty catheter 12 in accordance with a first embodiment. As is described in the Packard, et al patent application, Ser. No. 822,385, filed Jan. 27, 1986 and assigned to the assignee of the present invention, the catheter 12 may comprise an outer flexible plastic tubular member having a proximal end 14 and a distal end 16 and mounted on the outer tubular member near its distal end is an expander member 18. Formed through the side wall of the tubular member 12 within the confines of the expander member 18 are one or more ports which communicate with the central lumen of the tube 12. Thus, by injecting a fluid through the lumen and by blocking the distal end 16, the fluid flows through the ports to inflate the expander 18. In that the catheter 12 with which the present invention is used is fully described in the aforementioned patent application, it is deemed unnecessary to described further the make-up of the catheter device.

Figure 3:
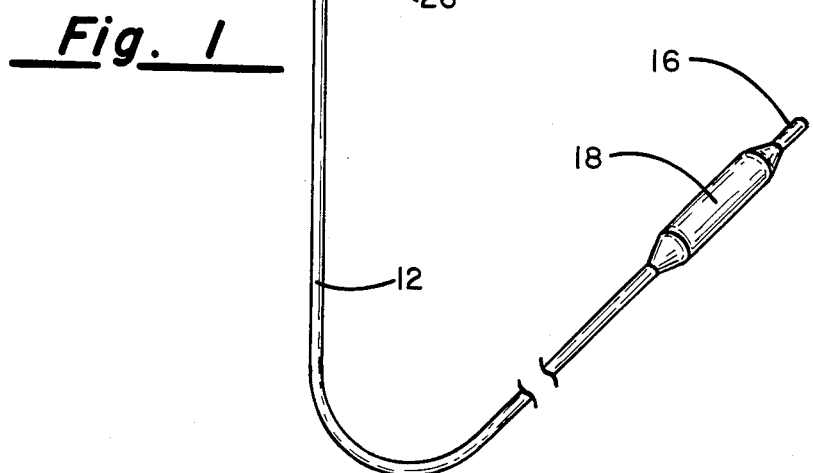
FIG. 3 is a cross-sectional view taken along the lines 3—3 in FIG. 2.
Figure 3:
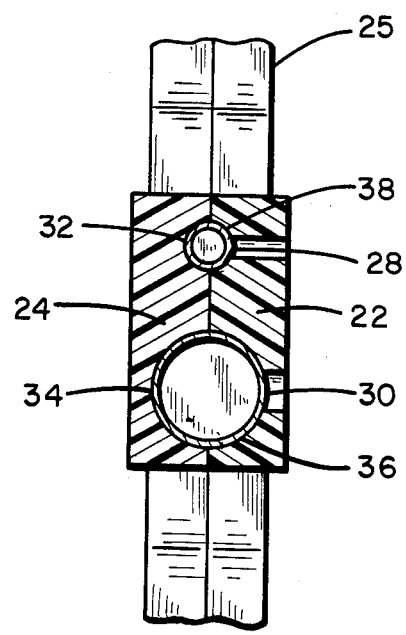

The inflation device 10 comprises a two-piece, molded plastic housing which is indicated generally by numeral 20 and which is composed of a first housing half 22 and a second housing 24 which are fastened together by screws as at 26. Formed interiorly of the housing halves 22 and 24 are semi-cylindrical recesses such as recesses 28 and 30 in housing half 22 and recesses 32 and 34 in housing half 24. As can be seen in FIG. 3, when the housing halves are joined together, the semi-circular recess 30 in housing half 22 is longitudinally aligned with the semi-circular recess 34 in housing half 24. The same holds true for the recesses 28 and 32 which, together, form a cylindrical opening. These cylindrical openings are adapted to receive hypodermic-type syringes. For example, a relatively large volume and diameter syringe 36 may be contained in the circular opening defined by the recesses 30 and 34 while a smaller diameter and volume syringe 38 may be contained in the opening defined by the recesses 28 and 32. By way of example only, the syringe 36 may have a volume of 10 cc and, as such, has an outside diameter of approximately 6.5 cm. The syringe 38, on the other hand, may have a 2 cc capacity and an outside diameter of 3.0 cm.

As can be seen in FIG. 2, the syringes 36 and 38 have graduated markings along the barrel thereof and one or the other of the housing halves 22 or 24 is provided with a window in the form of a longitudinal slit 40 through which the graduations on the syringe 36 may be viewed. Similarly, a longitudinally extending slot 42 allows the graduated markings on the syringe 38 to be viewed.

The syringes 32 and 38 are conventional in their construction and are generally comprises of a glass or plastic tubular cylinder containing a piston made from an elastomeric material, the piston being secured to the end of a plunger, such as plunger 44 of the hypodermic syringe 36 and plunger 46 of the hypodermic syringe 38. At the distal end of each of the hypodermic syringes is an outlet port surrounded by a coupling device such as a Luer connector. The connector provides a fluid-type seal with short lengths of tubing 48 and 50 leading to a three-way valve device indicated generally by numeral 52. The valve 52 is arranged to fit within a molded recess formed in the housing halves 22 and 24 so as to be clamped snugly in place when the screws 26 are used to join the housing halves together. The valve 52 has a first inlet thereof joined to the tubing element 48 leading to the outlet of the small capacity syringe 38. A second inlet to the valve 52 is coupled to the outlet port of the large capacity syringe 36. The valve's outlet 58 is suitably coupled to the proximal end 14 of the catheter 12.

The valve 52 also comprises an outer barrel 60 comprising the valve body and an internal, generally solid cylinder which is rotatably and sealingly disposed within the housing 60. The internal cylinder can be rotated by means of a handle member 62 which extends outwardly of the housing 20. Formed in the rotatable cylindrical member are first and second bores which intersect to form a "T". Thus, when the lever 62 is in a first position, there is a direct fluid conducting path through the valve from the inlet 56 to the outlet 58. This, of course, allows fluid from the large capacity syringe 36 to be initially injected into the lumen of the catheter 12 so as to fill that lumen with fluid as well as to fill the balloon 18 when the plunger 44 is depressed. Then, when the handle 62 is rotated 90°, a flow path is established between the valve inlet 54 and the outlet 58 whereby fluid from the small capacity syringe 38 may be forced out the outlet 58 when the plunger 46 is depressed. Finally, when the valve handle 62 is moved to a third disposition, a fluid conducting path is established between the inlet ports 54 and 56 of the valve whereby fluid contained within the large capacity syringe 36 may be drawn into the small capacity syringe 38 and vice versa by appropriately manipulating the plungers on each. This allows the small capacity syringe to be filled from the large capcity syringe acting as a reservoir.

As is shown in the perspective view of FIG. 1, there is also mounted on the housing 20 a pressure gauge 64 which communicates with the outlet port 58 of the three-way valve so that the user is in a position to measure the hydraulic pressure existing within the catheter body. The scale on the pressure gauge 64 is marked to reflect both pounds per square inch and number of atmospheres.

OPERATION—FIRST EMBODIMENT

As is pointed out in the aforereferenced Schjeldahl Patent No. 4,413,989, in treating a stenotic lesion in the cardiovascular system, a small incision is made at an appropriate location to gain access to the appropriate blood vessel to be treated and the catheter 12 is advanced through the vascular system until the expander member 18 is disposed at the site of the lesion to be treated. Prior to the dilation of the stenotic lesion, a mixture of saline solution and a contrast medium, such as 50% Renagrafin 76 may be perfused through the catheter and out its distal end 16, so that the site to be treated can be viewed fluoroscopically, by positioning the valve arm 62 such that the contents of the large volume syringe 36 can flow through the catheter 12. Once it has been determined that the expander member 18 has been properly positioned relative to the stenotic lesion to be treated, the valve arm 62 may be rotated such that the small volume, small diameter syringe 38 is in fluid communication with the catheter 12. Because the diameter of the piston in the low volume syringe 38 is small relative to that of the large volume syringe 36, a higher pressure in terms of pounds per square inch or kilograms per square centimeter can be generated with a lower force being applied to the plunger 46. Thus, the expander member 18 can be inflated to a pressure in the range of from 7 to 8 atmospheres by depressing the plunger 46 and can be held for a predetermined time without undue muscle fatigue and involuntary movement of the hand and arm of the cardiologist.

To replenish the level of fluid contained within the small volume syringe 38, the handle 62 on the valve 52 can be moved to its third position wherein fluid communication is established in the outlet 50 of the syringe 36 and the outlet of the small volume syringe 38. Thus, by drawing back on the plunger 46, fluid will be drawn from the large reservoir maintained in the syringe 36 and into the small diameter syringe 38.

During the procedure, of course, the cardiologist or his technician can monitor the balloon pressure using the pressure gauge 64.

ALTERNATE PREFERRED EMBODIMENT

In accordance with the alternative embodiment of the invention, the low pressure, high volume syringe is positioned generally coaxially with the lower volume, high pressure dilation syringe. Referring to FIG. 4, there is shown generally by numeral 70 and angioplasty catheter inflation and perfusion syringe having an outer tubular body 72 formed of glass, plastic or other suitable material, the body having a relatively large diameter portion 74 and a smaller diameter portion 76 integrally formed therewith, the two portions being joined by a frustoconical shaped transition 78.

Extending radially outwardly from the side walls of the outer tubular portion 74 near its proximal end are finger grips 80 and 82, the purpose of which will become apparent as the description of the embodiment of FIG. 4 continues.

Disposed at the distal end of the smaller diameter portion 76 of the inflation syringe 70 is a complex block 84 for joining the syringe 70 to the proximal end of an angioplasty catheter, only a portion of which is illustrated and which is identified by numeral 86. Again, the catheter 86 preferably is of the type described in the Packard et al application referenced earlier. The coupler 84 also has an annular port 88 leading from the bore 90 which joins the outlet of the syringe 70 to the catheter 86 and to a suitable pressure indicator 92 which is preferably calibrated to indicate the hydraulic pressure in the system in both units of pounds per square inch and in atmospheres.

Positioned within the cylindrical bore of the relatively large diameter syringe 74 is a piston 94 which is affixed to one end of a plunger tube 96. The piston 94 is formed from a suitable elastomeric material and is configured as shown in FIG. 5 to provide a fluid-tight seal with the inner wall surface of the larger diameter syringe 74 and with a cylindrical plunger rod 98 which is slidingly received within the lumen of the tubular plunger member 96.

Attached to the distal end of the plunger rod 98 is a second piston member 100 which is configured to provide a fluid-tight seal with the inner wall surface of the smaller diameter syringe portion 76.

Integrally formed with or otherwise affixed to the proximal end of the plunger tube 96 is a smoothly rounded knob 102 which is intended to interact with the palm of the hand of the user so that by simultaneously gripping the finger grips 80 and 82 with the index and middle fingers, a force can be applied to the knob 102 to advance the plunger 96 and its associated piston 94 to force liquid out of the syringe assembly 70 and through the catheter 88. Similarly, by pulling back on the knob 102 in the proximal direction, the fluid contained within the catheter 86 can be aspirated, i.e., drawn hack into the syringe.

Formed through the side wall of the plunger tube 96 is a longitudinal slot 104. A suitable knob 106 is loosely fitted about the outside diameter of the plunger rod 96 and a pin 108 is used to join the knob 106 to the end portion of the plunger rod 98. The pin is of a diameter such that it can readily slide back and forth within the confines of the slot 104 formed in the plunger tube 96. Thus, by manipulating the knob 106, the user can force the piston 100 into the bore of the smaller diameter syringe portion 76.

It has also been found expedient to provide a relief groove in the internal surface of the syringe body at the entry point of the smaller diameter piston 100 so that that piston will be fitted into the smaller bore of the syringe portion 76 before a substantial pressure can be created by the further advancement of that piston 100 as the knob 106 is pushed in a distal direction. The relief groove serves as a vent which prevents substantial pressure build-up until the piston 100 is full into the smaller bore of the syringe portion 76.

While not shown in FIG. 4, it is contemplated that the syringe barrel 74 and 76 be provided with suitable gradations on the barrel to facilitate the monitoring of fluid content. Also, by way of illustration and with no limitation intended, the larger diameter syringe portion 74 may be dimensioned so as to contain around 10 cc. of fluid while the smaller diameter portion 76 is dimensioned to contain approximately 2 cc. It should also be apparent to those skilled in the art that the high and low pressure plungers can be reverse from what is illustrated in FIG. 4 so that it would be the high pressure plunger which extends most proximally rather than the low pressure plunger as set out in the drawing of FIG. 4.

FIG. 5 is a greatly enlarged perspective view of the elastomeric piston 94. The elastomeric piston preferably has a rounded anterior face 112 and which has at least one, but preferably two, annular notches 114 formed in its side surface to define a plurality of ribs 116. The bore 118 through which the plunger rod 98 is arranged to pass is also provided with similar annular grooves to define separated rib surfaces (not shown). Using this construction, when pressure is applied by advancing the knob 102 relative to the syringe body, the rounded surface 112 tends to flatten and thus expand the diameter of the elastomeric plunger so that the ribs 116 and the internal ribs within the bore 118 (not shown) wipe firmly against the mating surfaces with which they cooperate to provide a fluid-type seal but while still permitting sliding motion between its mating parts.

SECOND ALTERNATE PREFERRED EMBODIMENT

In accordance with a futher alternative embodiment of the invention, the low pressure, high volume syringe is again positioned generally coaxially with the lower volume, high pressure dilation syringe. More particularly, referring to FIG. 6, there is shown generally by numeral 120, an angioplasty catheter inflation and perfusion syringe somewhat similar in its construction to the embodiment of FIG. 4. It includes an outer tubular body 72 formed of glass, plastic or other suitable material which has a relatively large diameter section 74 integrally joined with a section 76 of a lesser diameter by way of a frustoconical shaped transition section 78. Secured to the proximal end of the larger diameter tubular segment 74 is a generally cylindrical molded plastic sleeve 122 having radially outwardly extending flange-like projections 124 and 126 which serve as finger grips.

Connected to the distal end of the smaller diameter syringe segment 76 of the inflation syringe 120 is a coupler block 84 which is used to join the outlet end of the syringe to the proximal end of an angioplasty catheter 86. A port 88 serves to couple the interior of the coupler 88 to a suitable pressure indicator 92.

As with the embodiment of FIG. 4, the device of FIG. 6 is also seen to include a piston 94 positioned within the cylindrical bore of the larger diameter syringe segment 74 and it is affixed to the distal end of a plunger tube 96. Again, the piston element 94 is preferably formed from a suitable elastomeric material and may be configured as shown in FIG. 5. As such, it is arranged to provide a fluid-type seal with the inner wall surface of the larger diameter syringe 74 as well as with the outside diameter of a cylindrical plunger rod 98 which is slidingly received within the lumen of the tubular plunger member 96. An elastomeric piston 100 is joined to the distal end of the plunger rod 98 and is suitably configured to provide a fluid-type seal with respect to the inside wall of the lower diameter segment 76 of the syringe 120.

A smoothly rounded plastic or elastomeric knob member 102 is affixed to the proximal end of the piston rod 96 and the dimensions are such that the knob 102 fits the contour of the user's palm when the forefinger and index finger are partially wrapped about the finger grip elements 124 and 126. Thus, by squeezing, the plunger 96 and its associated piston 94 are urged distally to thereby force liquid out of the syringe assembly 120 and through the catheter 86.

Formed through the side wall of the plunger tube 96 and identified by numeral 104 is an elongated, longitudinally extending slot. Surrounding the tube 96 is a molded plastic sleeve member 128 whose end surface 130 thereof is knurled so as to facilitate the gripping and rotation thereof. The sleeve 128 loosely fits about the exterior of the plunger shaft 96 and is free to rotate about it. Formed in the exposed exterior surface of the sleeve 128 is a helical groove 132 into which is fitted a pin 134 secured to the finger grip member 122. As can best be seen in FIG. 7, the plunger tube 98 also has a radially projecting pin 136 which is arranged to fit within a helical groove formed on the interior wall of the rotatable sleeve 128. The pin 136 passes through the longitudinal groove 104 formed in the outer plunger tube 96.

With the foregoing construction, it is apparent that, when the knob 102 is pushed in the distal direction, the piston 94 moves independently of the piston 100. Thus, the contents of the larger diameter syringe segment 74 can be displaced out the connector block 88 and used to fill the body of the catheter 86. Next, by rotating the knurled sleeve 128, the coaction between the helical groove 132 and the stationary pin 134 will cause the member 128 to be translated in either the distal or proximal direction, depending upon the direction of rotation of the member 128. Because the pin 136 attached to the plunger 98 is received within the annular groove 138, the rotation of the knob 128 results in a corresponding displacement of the piston 100 which, when it enters the lower diameter segment 76, results in a substantial increase in the fluid pressure contained within the system, assuming that the system has been previously filled with fluid from the larger diameter syringe portion 74.

The substitution of the rotatable sleeve 128 for the grip member 106 in the embodiment of FIG. 5 allows the pressure setting to be maintained following release of the surgeon's fingers from the adjustment knob 128. That is to say, the piston 100 will be held in place even when the adjustment knob 128 is no longer gripped.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An inflation device for a transluminal angioplasty catheter of the type including an elongated tubular member having a proximal end and a distal end, said tubular member supporting an expander member proximate said distal end, said inflation device comprising in combination:
   (a) a syringe housing having at least two coaxially and longitudinally aligned cylindrical cavities of differing diameter for individually receiving a first, relatively large diameter piston and a second relatively low diameter piston forming first and second syringes, respectively;
   (b) first and second plunger members connected to said first and second pistons for applying displacement forces thereto, said second plunger member being slidingly received within a longitudinal bore formed in said first plunger member and including a portion which extends outwardly beyond the end of said first piston toward said second syringe; and
   (c) means coupling said first and second syringes to said proximal end of said angioplasty catheter such that when said first plunger is actuated a fluid is displaced from said first syringe through said second syringe and into said catheter and when said second plunger is actuated within said second syringe, a greater fluid pressure is created within said catheter than when said first plunger is actuated.

2. The inflation device as in claim 1 wherein said first plunger member is tubular and contains said second plunger member in the longitudinal bore thereof for reciprocating motion.

3. The inflation device as in claim 1 wherein said first plunger member has a longitudinal slot through the tubular wall thereof and further includes a grippable memeber secured to said second plunger member through said slot.

4. The inflation device as in claim 1 wherein said first and second pistons have a ribbed exterior surface for cooperating with the side walls of said first and second cavities, respectively.

5. The inflation device as in claim 1 and further including a pressure indicator joined to said coupling means for indicating the fluid pressure existing within said system.

6. The inflation device as in claim 1 and further including a rotatable sleeve surrounding said first plunger member, said sleeve being provided with a helical groove cooperating with a mating projection on said housing and operatively coupled to said second plunger member whereby rotation of said sleeve relative to said housing causes longitudinal displacement of said second plunger member.

* * * * *